United States Patent [19]

Thompson

[11] Patent Number: 5,130,418
[45] Date of Patent: Jul. 14, 1992

[54] METHOD TO STABILIZE BASIC FIBROBLAST GROWTH FACTOR

[75] Inventor: Stewart A. Thompson, Mountain View, Calif.

[73] Assignee: California Biotechnology Inc., Mountain View, Calif.

[21] Appl. No.: 346,431

[22] Filed: May 2, 1989

[51] Int. Cl.$^5$ .................. C07K 7/10; C07K 13/00
[52] U.S. Cl. .................. 530/399; 530/350; 530/402
[58] Field of Search .......... 514/12, 970, 973; 530/399, 402, 350

[56] References Cited

U.S. PATENT DOCUMENTS 4,816,561 3/1989 Todaro .................. 530/325

FOREIGN PATENT DOCUMENTS 0178665 4/1986 European Pat. Off. .

OTHER PUBLICATIONS

Ahmed, *The Journal of Biological Chemistry*, 250, No. 21, 8477–8482, 1975.
Seno et al., *Biochem. Biophys. Res. Comm.* (1988) 151:701.
Esch et al., *Proc. Natl. Acad. Sci. U.S.A.* (1985) 82:6507.
Eagle et al., *J. Biol. Chem.* (1986) 235(6):1719–1726.
King *J. Biol. Chem.* (1961) 236(2):PC5.
Huisman et al., *J. Lab. Clin. Med.* (1962) 60(2)302–319.
Harrap et al., *Biochim. Biophys. Acta* (1973) 310:104–110.
Isaacs et al., *Biochim. Biophys. Acta* (1977) 497:192–204.
Mannervitc et al., *Biochim. J.* (1980) 190:125–130.
Fox et al., *J. Biol. Chem.* (1988) 263:18452.
Story et al., *Biochem. Biophys. Res. Comm.* (1987) 142 (3):702–709.

*Primary Examiner*—F. T. Moezie
*Attorney, Agent, or Firm*—Morrison & Foerster

[57] ABSTRACT

Treatment of basic fibroblast growth factor (bFGF) with organic disulfides, preferably glutathione disulfide, or with inorganic compounds of similar function results in a bFGF composition of enhanced stability and resistance to multimerization. The resulting stabilized form mimics the chromatographic behavior of bFGF as isolated from bovine pituitary.

7 Claims, 11 Drawing Sheets

```
                                    1
                                    ATG GCC GCC GGG AGC ATC ACC ACG CTG
                                   (Met Ala Ala Gly Ser Ile Thr Thr Leu)
                                    -9                                 -1
        10                                  20
CCA GCC CTG CCG GAG GAC GGC GGC AGC GGC GCT TTC CCG CCG GGC CAC
Pro Ala Leu Pro Glu Asp Gly Gly Ser Gly Ala Phe Pro Pro Gly His
 1                                  10
                    30                                          40
TTC AAG GAC CCC AAG CGG CTG TAC TGC AAG AAC GGG GGC TTC TTC CTG
Phe Lys Asp Pro Lys Arg Leu Tyr Cys Lys Asn Gly Gly Phe Phe Leu
                    20                                          30
                                    50
CGC ATC CAC CCC GAC GGC CGA GTG GAC GGG GTC CGC GAG AAG AGC GAC
Arg Ile His Pro Asp Gly Arg Val Asp Gly Val Arg Glu Lys Ser Asp
                                    40
            60                                          70
CCA CAC ATC AAA CTA CAA CTT CAA GCA GAA GAG AGA GGG GTT GTG TCT
Pro His Ile Lys Leu Gln Leu Gln Ala Glu Glu Arg Gly Val Val Ser
            50                                          60
                            80
ATC AAA GGA GTG TGT GCA AAC CGT TAC CTT GCT ATG AAA GAA GAT GGA
Ile Lys Gly Val Cys Ala Asn Arg Tyr Leu Ala Met Lys Glu Asp Gly
                            70                                  80
 90                                     100
AGA TTA CTA GCT TCT AAA TGT GTT ACA GAC GAG TGT TTC TTT TTT GAA
Arg Leu Leu Ala Ser Lys Cys Val Thr Asp Glu Cys Phe Phe Phe Glu
                            90
                    110                                 120
CGA TTG GAG TCT AAT AAC TAC AAT ACT TAC CGG TCA AGG AAA TAC TCC
Arg Leu Glu Ser Asn Asn Tyr Asn Thr Tyr Arg Ser Arg Lys Tyr Ser
                    100                                 110
                                130
AGT TGG TAT GTG GCA CTG AAA CGA ACT GGG CAG TAT AAA CTT GGA CCC
Ser Trp Tyr Val Ala Leu Lys Arg Thr Gly Gln Tyr Lys Leu Gly Pro
                                120
            140                                         150
AAA ACA GGA CCT GGG CAG AAA GCT ATA CTT TTT CTT CCA ATG TCT GCT
Lys Thr Gly Pro Gly Gln Lys Ala Ile Leu Phe Leu Pro Met Ser Ala
            130                                         140
        155
AAG AGC TGA TCT TAA
Lys Ser Ter     Ter
        146
```

FIG.8

```
                                      1
                                      ATG GCA GCC GGG AGC ATC ACC ACG CTG
                                     (Met Ala Ala Gly Ser Ile Thr Thr Leu)
                                      -9                                -1
    10                                                 20
    CCC GCC TTG CCC GAG GAT GGC GGC AGC GGC GCC TTC CCG CCC GGC CAC
    Pro Ala Leu Pro Glu Asp Gly Gly Ser Gly Ala Phe Pro Pro Gly His
     1                                            10
                            30                                        40
    TTC AAG GAC CCC AAG CGG CTG TAC TGC AAA AAC GGG GGC TTC TTC CTG
    Phe Lys Asp Pro Lys Arg Leu Tyr Cys Lys Asn Gly Gly Phe Phe Leu
                     20                                    30
                                      50
    CGC ATC CAC CCC GAC GGC CGA GTT GAC GGG GTC CGG GAG AAG AGC GAC
    Arg Ile His Pro Asp Gly Arg Val Asp Gly Val Arg Glu Lys Ser Asp
                                      40
            60                                                 70
    CCT CAC ATC AAG CTA CAA CTT CAA GCA GAA GAG AGA GGA GTT GTG TCT
    Pro His Ile Lys Leu Gln Leu Gln Ala Glu Glu Arg Gly Val Val Ser
                 50                                       60
                                 80
    ATC AAA GGA GTG TGT GCT AAC CGT TAC CTG GCT ATG AAG GAA GAT GGA
    Ile Lys Gly Val Cys Ala Asn Arg Tyr Leu Ala Met Lys Glu Asp Gly
                              70                                    80
    90                                                 100
    AGA TTA CTG GCT TCT AAA TGT GTT ACG GAT GAG TGT TTC TTT TTT GAA
    Arg Leu Leu Ala Ser Lys Cys Val Thr Asp Glu Cys Phe Phe Phe Glu
                                      90
                            110                                       120
    CGA TTG GAA TCT AAT AAC TAC AAT ACT TAC CGG TCA AGG AAA TAC ACC
    Arg Leu Glu Ser Asn Asn Tyr Asn Thr Tyr Arg Ser Arg Lys Tyr Thr
                     100                                   110
                                   -  130
    AGT TGG TAT GTG GCA TTG AAA CGA ACT GGG CAG TAT AAA CTT GGA TCC
    Ser Trp Tyr Val Ala Leu Lys Arg Thr Gly Gln Tyr Lys Leu Gly Ser
                                      120
            140                                                150
    AAA ACA GGA CCT GGG CAG AAA GCT ATA CTT TTT CTT CCA ATG TCT GCT
    Lys Thr Gly Pro Gly Gln Lys Ala Ile Leu Phe Leu Pro Met Ser Ala
                130                                           140
            155
    AAG AGC TGA TTT TAA
    Lys Ser Ter     Ter
            146
```

FIG.9

METHOD TO STABILIZE BASIC FIBROBLAST GROWTH FACTOR

TECHNICAL FIELD

The invention relates to the field of stabilizing protein compositions. More specifically, it concerns procedures for stabilizing basic fibroblast growth factor by treatment with disulfides or other compounds capable of forming S—S covalent bonds.

BACKGROUND ART

One of the persistent problems involved in the recombinant production of desired proteins resides in the obtainment of proper processing and folding of the recombinant product. Because the gene encoding the primary protein structure is generally expressed in a host system foreign to that in which it is normally transcribed and translated, the resultant product protein, while having the correct amino acid sequence, has different characteristics from the native protein. In some instances, a part of this difference resides in a change in molecular structure—most commonly, lack of normally associated glycosylation. However, it is also understood that the three-dimensional conformation of the protein may be different depending on the cellular environment. In particular, various recombinant hosts are thought to have differing environments with respect to the level of oxidation or reduction that normally is associated with the cellular components, resulting in recombinant proteins with disulfide bond compositions which differ from those of the native protein, and, in general, altered three-dimensional dimensional structures. These alterations may have deleterious effects on behavior and activity.

In the case of basic fibroblast growth factor (bFGF), glycosylation patterns are not germane as the native molecule is unglycosylated. However, recombinantly produced material differs from that isolated from pituitaries in its chromatographic behavior and poses stability problems unless measures are taken to prevent multimerization in solution. It has been shown, by applicant herein, and as disclosed by Seno, M., et al., *Biochem Biophys Res Comm* (1988) 151:701, that substitution of serine for the cysteines at positions 78 and 96 prevents multimerization. It is also the case that bFGF isolated from natural bovine pituitary does not multimerize.

It has been disclosed that amino acid composition determinations of native isolated bovine bFGF indicate the presence of six cysteines, although the gene encodes only four. It was proposed that additional residues of cysteine might be disulfide linked to the protein (Esch, F., et al., *Proc Natl Acad Sci USA* (1985) 82:6507).

The formation of conjugates of cysteine or glutathione with proteins by reaction with cystine or glutathione disulfide as a natural phenomenon has long been suggested and disclosed. In 1960, Eagle, H. et al., *J Biol Chem* (1960) 235:1719–1726 showed that mammalian cell cultures were abetted by addition of compounds capable of forming S—S covalent bonds including, e.g., cysteine, $S_2O_3^{-2}$, and thioglycolate. The authors concluded that the proteins in the medium were bound by S—S bonds to these reagents. Human serum albumin was disclosed to exist in a dimerized form, presumably disulfide bonded, and in a monomeric form stabilized by cysteine or glutathione by King, T. P., *J Biol Chem* (1961) 236:PC5. Binding to glutathione was proposed to account for the heterogeneity of hemoglobin by Huisman, T. H. et al., *J Lab & Clin Med* (1962) 60:302–319.

Hanap, K. R. et al., *Biochim Biophys Acta* (1973) 310:104–110 acknowledged the presence of mixed disulfides of glutathione and serum albumin and found them reducible by glutathione reductase. Isaacs, J. et al., *Biochim Biophys Acta* (1977) 497:192–204 propose formation of mixed disulfides of proteins with glutathione as a means to regulate S—S/SH ratio. Conversely, Mannervitc, B. et al., *Biochim J* (1980) 190:125–130 postulate the formation of disulfides with proteins to represent a mechanism for regulation of protein activity. Pyruvate kinase is used as an example.

It has also been proposed, because of the conservation of cysteines at residues 34 and 101 in the genes encoding bFGF in various mammals, that an intramolecular disulfide is formed between these two residues, and the formation of this disulfide in the recombinant mutant form of bFGF having serine substituted for cysteine at positions 78 and 96 has been reported (Fox, G. M., et al., *J Biol Chem* (1988) 263:18452).

It has now been found that addition of an organic disulfide-containing compound, such as glutathione disulfide, to preparations of recombinantly produced bFGF results in enhanced stabilization and behavior more closely related to the native protein. Purification of this stabilized form of bFGF results in a preparation suitable for formulation for pharmaceutical applications.

DISCLOSURE OF THE INVENTION

The invention provides basic fibroblast growth factor (bFGF) in a form which is stable, convenient, similar to the native protein in activity, and adaptable to pharmaceutical formulations. This form is obtained by treating a susceptible form of basic fibroblast growth factor or its analogs with a protective agent capable of forming a covalent S—S bond with bFGF, such as an organic disulfide, e.g. glutathione disulfide (GSSG). The thus-stabilized bFGF can then be further purified using standard chromatographic techniques for use in pharmaceutical or other compositions.

Thus, in one aspect, the invention is directed to a method to stabilize bFGF protein which method comprises treating a susceptible peptide having the amino acid sequence of bFGF with an amount of a protective agent capable of forming a covalent S—S bond with bFGF, preferably a compound of the formula RSSR wherein R is an organic moiety, effective to prevent multimerization, in the presence of a buffer of pH 6 or greater, and at which the bFGF does not denature, for a time sufficient to effect said stabilization.

In other aspects, the invention is directed to bFGF prepared according to the methods of the invention and to the compositions useful in the invention method.

MODES OF CARRYING OUT THE INVENTION

As used herein, basic fibroblast growth factor is defined as a protein which is a cation at pH 7 and which is capable of mitogenic activity in in vitro assays using cultured cells, such as bovine brain and adrenal cortex-derived capillary endothelial (ACE) cells, human umbilical vein endothelial cells, bovine adrenal cortex cells, granulosa cells, or vascular smooth muscular cells. In vitro assays employing these cell cultures have been described by Gospodarowicz, D. et al., *J Cell Physiol* (1985) 122:323-332, Gospodarowicz, D. et al., *J Cell Biol* (1983) 97:1677-1685, Esch et al., *Proc Natl Acad Sci USA* (1985) 82:6507-6511 and Gospodarowicz, D. et al., *J Cell Physiol* (1986) 127:121-136. In addition, in vivo assays using chicken chorioallantoic membrane have also been described by Gospodarowicz, D. in "Hormonal Protein and Peptides" XII:205-230 (Academic Press). A protein which is a cation at pH 7 and which has activity in at least one of these assays is defined as basic FGF.

Figure 8:
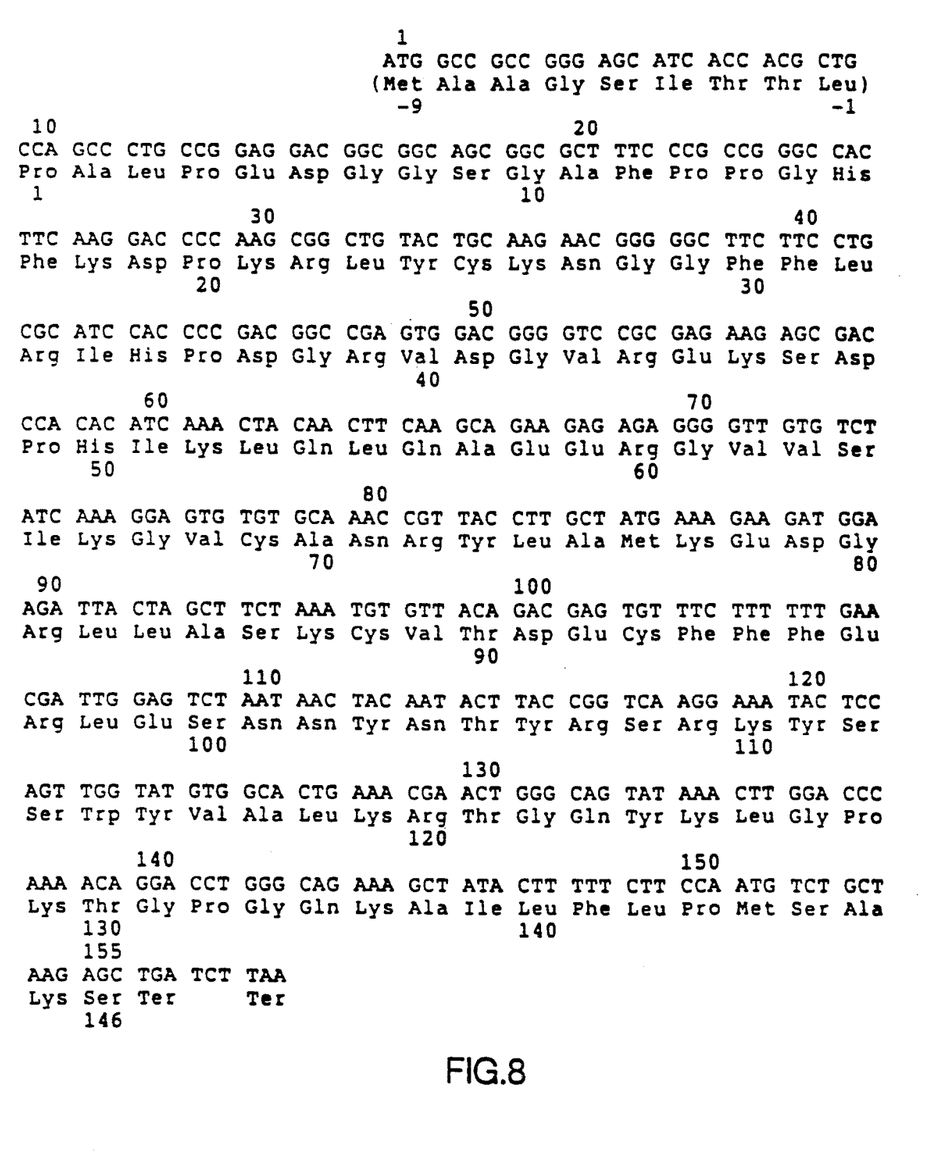
FIGS. 8 and 9 give the DNA coding sequences for, and deduced amino acid sequences of, bovine and human basic FGF, respectively.
Figure 9:
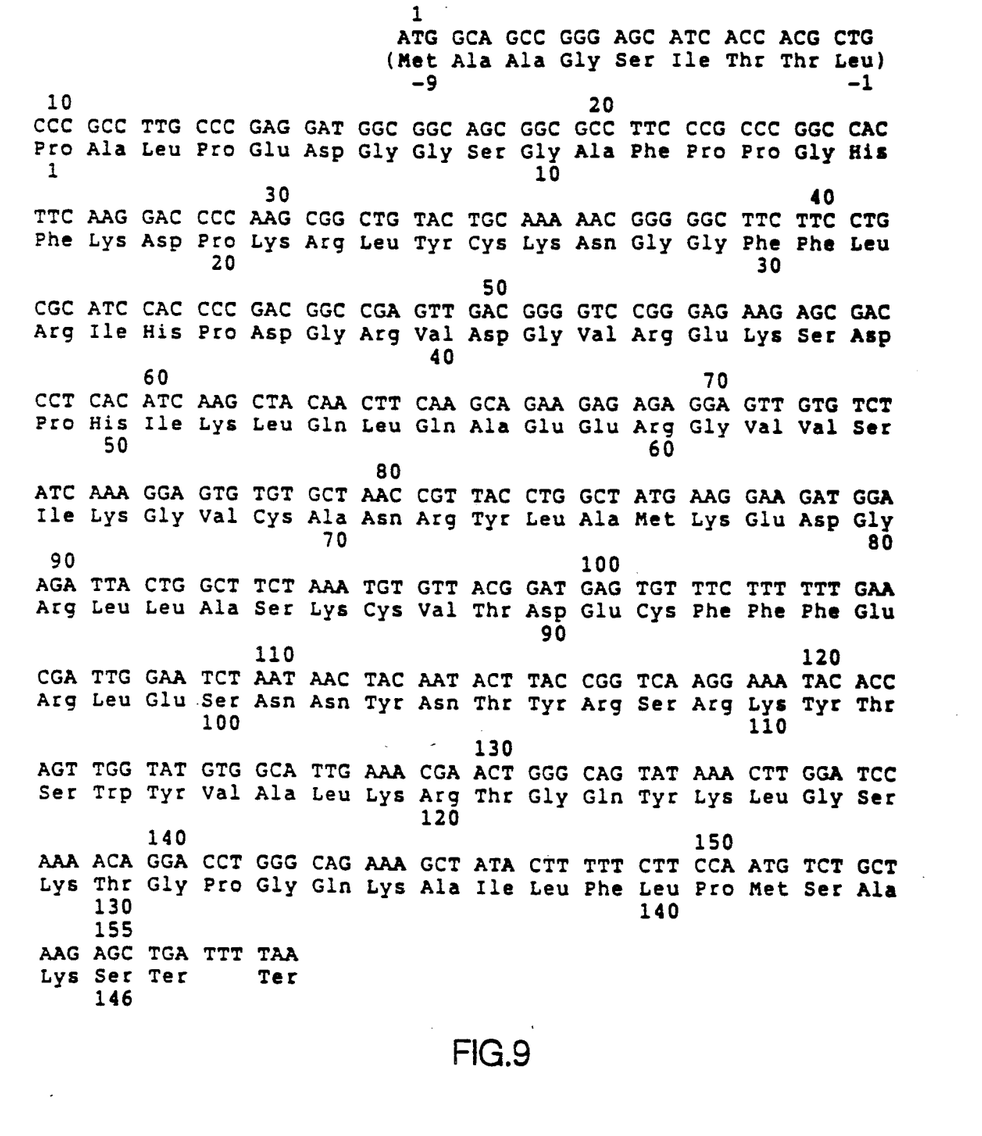

The amino acid sequences fulfilling this definition are of various embodiments. Preferred embodiments are shown in FIGS. 8 and 9, which indicate the amino acid sequences of the basic FGFs encoded by genes isolated from bovine and human libraries, respectively. These genes encode proteins of the form generally isolated from, e.g., pituitary, having 146 amino acids, beginning with the proline residues numbered "1" below the sequences in the Figures. The indicated human and bovine 146 amino acid sequences are two preferred embodiments of the basic FGF to which the method of the invention is applicable. Also preferred are active forms of the proteins shown in FIGS. 8 and 9 which include N-terminal extensions of the 146 amino acid sequence, as there shown, as well as N-terminal shortened forms of these sequences lacking as many as 15 amino acids from the 146 amino acid sequence. Particularly preferred are the forms containing all seven or eight upstream amino acids shown exclusive of the N-terminal methionine (which is removed during production of recombinant bFGF in bacteria), for a total of 153 or 154 amino acids, and a shortened form lacking the first 15 amino acids of this basic sequence, containing 131 amino acids. When the protein is produced recombinantly, the 154 amino acid form results from expression of the complete 155 amino acid sequence which is followed by removal of the Met by post-translational processing. Most preferred are the 153 or 154 amino acid forms beginning with the ala residues shown as positions 2 or 3 in the numbering above the sequences, or mixtures thereof. In general, the numbering system used herein is that corresponding to the overplaced numbers.

Most, but not all, proteins which fall under the definition of basic FGF, besides showing FGF activity in at least one of the foregoing assays and being cations at neutral pH, bind to heparin and react immunologically with antibodies prepared using a synthetic analog of the amino terminal sequence or to other antibodies raised against bovine or human basic FGF or synthetic or native peptide fragments thereof, as appropriate. Generally, these proteins are at least 80% homologous with the bFGF proteins of FIGS. 8 or 9, preferably 90% homologous. Among preferred embodiments are analogs of bFGF which retain FGF activity in the foregoing assays. In order to be a suitable substrate in the method of the invention, the bFGF should include cysteine capable of forming a covalent —S—S—bond, e.g. one, and preferably two cysteine residues in positions other than those involved in the (putative intramolecular disulfide linking) positions 34 and 101.

In general, the method of the invention is applicable to any "susceptible" bFGF protein, which forms disulfide bonded multimers in the absence of antioxidants. The propensity of a protein to form multimers can be assessed readily by, for example, subjecting a preparation of the protein which is exposed to air for various times to standard high performance chromatography methods to detect the presence of higher molecular weight forms. Alternatively, multimerization can be detected by subjecting these preparations to SDS-PAGE under reducing and nonreducing conditions. The results under reducing conditions provide the standard nonmultimerized molecular weight; nonreduced materials will show the presence of multimers. For proteins which multimerize under this regimen, stabilization of the nonmultimerized form can be obtained using the method of the invention.

Usually, proteins which multimerize contain at least one cysteine residue which is not involved in intramolecular disulfide linkages. Of course, it is not possible, by simply assessing the number of cysteines in the amino acid sequence, to discern whether the protein in question is susceptible to stabilization by this method, since examination of the sequence does not permit prediction of the extent to which intramolecular disulfides are formed. However, it has been shown by the inventors herein that, for example, acidic FGF, which has some homology to basic FGF, has similar activity, and is an anion at neutral pH, does not multimerize, nor does it react with GSSG. This shows that "susceptibility" is not obvious from amino acid sequence but must be determined experimentally. Acidic FGF has an odd number of cysteines, so that formation of intramolecular disulfide leaves one free cysteine, and the protein is capable, therefore, of dimerization.

It is appropriate, therefore, to define the meaning of "susceptible" bFGF proteins—these are bFGF proteins which can be stabilized by the method of the invention, as shown by the assay described above. In the case of basic FGF, it is required, for susceptibility, that at least one of the cysteines at position 78 and/or 96 as shown in the overlined numbers of FIGS. 8 and 9 (or a cysteine corresponding to these, e.g., at a similar position in an analog) be present. It is more preferred that both cysteines be present. In order to maintain susceptibility, the precise positioning of these residues at the locations found in the native sequence is not necessary, and, in general, susceptible forms for basic FGF are those which have at least one, and preferably two cysteine residues available for multimerization, i.e. not contained, under the relevant conditions, in intramolecular disulfide bonds.

It is further noted that "native" basic FGF isolated from mammalian tissues is, under most published isolation protocols, already stabilized, presumably by indigenous glutathione disulfide available in situ. Basic FGF is susceptible to treatment to prevent multimerization only when produced under circumstances where this native stabilization does not occur. This occurs when an isolation protocol includes treatment of proteins with a reducing agent or most commonly in the recombinant production of basic FGF, especially in procaryotic systems, or in those eucaryotic systems which do not provide the correct environment for indigenous stabilization.

The Protective Agent

In general, the protective agents are reagents which are capable of forming a covalent S—S bond with a cysteine residue in the subject protein. Most commonly, the bond formed will be a disulfide bond, and the protecting agent will be of the formula RSSR, wherein each R is independently an organic residue which is sufficiently hydrophilic to permit water solubility. The most convenient embodiments of RSSR are those wherein both R residues are identical, as these are readily available in many instances and/or easily prepared from the component sulfhydryl compounds. For example, cystine, homocystine, cystamine, and glutathione disulfide (GSSG) are commonly available reagents. Mixed disulfides of these components could also be used, although there is no particular point in using the mixed disulfide. Also readily prepared, but very expensive, is the disulfide of coenzyme A.

It is seen from the foregoing exemplary compounds of the formula RSSR, that the nature of R is generally a hydrocarbyl with sufficient polar substitutions to permit water solubility. Thus, preferred embodiments for RSSR are those wherein the sulfur atom residue is a part of an amino acid or peptide, as in GSSG or cystine.

In addition to protective agents of the formula RSSR, inorganic compounds capable of forming a covalent S—S bond can be used. A convenient inorganic reagent is the salt of tetrathionate ion, i.e., $S_4O_6^-$. In this case, the stabilized form of the subject peptide will have a derivatized cysteine with a substituent of the formula —S—SO$_3^-$. Also usable as a protective agent is a mixed reagent of the formula RS—SO$_3^-$.

In summary, the protective agent can be any moiety which forms a covalent S—S bond with the sulfhydryl of a free cysteine in the substrate protein to be stabilized. Preferred in the stabilization of proteins intended for pharmaceutical use are reagents which generate pharmaceutically acceptable derivatives; therefore, use of compounds which derivatize the cysteine of the substrate with biologically compatible substances such as glutathione or cysteine are preferred.

General Method

The stabilization of the subject susceptible protein is conducted in a buffered aqueous solution. The pH may range between 6 and whatever upper limit is dictated by the stability of the protein with respect to denaturation. Any commonly employed buffer system which does not contain free sulfhydryl groups or thiol binding agents can be used, including phosphate buffer, Tris, and so forth. It may be desirable to add small concentrations of EDTA, about 1 mM, in order to prevent side reactions. The protein is dissolved in the buffer at a convenient concentration, depending on the solubility of the protein. Typical concentrations are in the range of 0.1–10 mg/ml. The protecting agent is employed at any convenient concentration, determined in part by the concentration of the subject protein employed. As the reaction is desired to proceed to completion, concentrations of reagent which result in a 10- to 100-fold molar excess over the amount of protein are desirable. Suitable amounts under many conditions of protein solute concentration are 0.1 mM–100 mM, or more usually 0.5–5 mM, depending on the solubility of the reagent. The reaction mixture is incubated for a time effective to confer stability, typically for a few hours to overnight, at a temperature of about 4° C. to about room temperature. The resulting stabilized protein is then purified using standard techniques. Depending on the choice of protecting agent, the protein is generally the only macromolecular substance in solution, and is thus easily recovered by gel filtration; other standard techniques may be used further to purify the protein. For example, if basic FGF is the subject protein, heparin sepharose affinity chromatography is conveniently used, as described by Gospodarowicz, D. et al., *Proc Natl Acad Sci USA* (1984) 81:6963.

The following examples are intended to illustrate, but not to limit, the invention.

PREPARATION A

Preparation of Recombinant bFGF

Human basic FGF was produced recombinantly in *E. coli*. The bFGF was recovered from the cell lysate and purified.

Briefly, and in particular, the human bFGF gene used encodes a 154 amino acid form of the protein beginning with the N-terminal sequence MetAlaGlySerIle. This bFGF gene has the sequence shown in FIG. 9, except that the ala at position 2 is deleted. When produced recombinantly, as described, in bacteria, the N-terminal methionine is processed off, yielding a homogeneous 153 amino acid form of the protein.

The gene was cloned into a standard procaryotic expression vector between the HindIII and EcoRI restriction sites and transformed into *E. coli* B. The culture was stored as a glycerol stock or on a plate of L+ampicillin.

A single colony was used to inoculate 50 ml of L-broth containing 50 ug/ml ampicillin and grown overnight at 30° C. 10 ml of this culture was used to inoculate 1 liter of M9 media containing 1×casamino acids and 50 ug/ml ampicillin. The culture was grown to an optical density of 0.5 at $A_{550}$ and induced with 50 ug/ml indole acrylic acid as the vector places the gene under control of the trp promoter. The culture was grown overnight at 30° C. In the morning the culture was centrifuged and the pellet was frozen at −78° C. until needed.

The pellet was resuspended in 25 ml of 20 mM Na phosphate pH 7, 1 mM EDTA, 1 mM phenylmethylsulfonyl fluoride and 0.5 mg/ml lysozyme. After 15 minutes on ice, the suspension was sonicated to rupture the cells. 100 ug each of RNAse and DNAse were added. After 10 minutes on ice, the mixture was centrifuged and the supernatant was saved for purification.

The supernatant was applied to a column of SP-Sephadex (2.5 cm×2 cm) equilibrated with 20 mM Na phosphate pH 7, 1 mM EDTA. The column was washed with the same buffer until the absorbance at 280 nm returned to baseline levels. The protein was eluted from the column with 20 mM Na phosphate pH 7, 1 mM EDTA, 400 mM NaCl.

The 400 mM NaCl bump from the SP-Sephadex column was loaded onto a column of heparin Sepharose (2.5 cm×2 cm) equilibrated with 20 mM Tris pH 7.5, 1 mM EDTA, 600 mM NaCl. The column was washed with the same buffer until the absorbance at 280 nm returned to baseline levels. The protein was eluted with 20 mM Na phosphate pH 7.5, 1 mM EDTA, 3 M NaCl.

The protein solution from the heparin Sepharose column was made 10 mM in DTT and incubated 30 minutes on ice, diluted 40 fold with 20 mM Na phosphate pH 7, 1 mM EDTA and repurified on SP-Sephadex as in the first step.

Alternatively, the protein is treated with DTT after the first SP-Sephadex column and then chromatographed on heparin-Sepharose as the final step. This procedure eliminates the need for the second SP-Sephadex column, but leaves the protein in a higher salt buffer.

EXAMPLE 1

Effect of GSSG Treatment of bFGF

The purified protein from Preparation A, which is the 153 amino acid human sequence of FIG. 9 missing met and one ala at the N-terminus, was then added at 0.1 mg/ml to 20 mM Sodium Phosphate buffer pH 7.5 containing 1 mM EDTA. The solution was then made 1 mM in glutathione disulfide and incubated overnight at 4° C. To maximize the conversion to the modified form, after 12 hr the solution was made 4 mM in GSSG, and incubated an additional 24 hr at 4° C. The resulting modified bFGF was purified on SP-Sephadex according to the method of Preparation A (supra).

FIGS. 1a-1d show the results of reverse phase HPLC run on Vydac $C_{18}$ column, 4.3 mm×25 cm 5 μm particle size 300 Å pore size in eluants A: 0.1% TFA, B: acetonitrile plus 0.1% TFA with a gradient ranging from 20% B for 40 minutes followed by 40% B for 5 minutes and at a flow rate of 1 ml/minute with absorbance read at 220 nm.

Figure 1A:
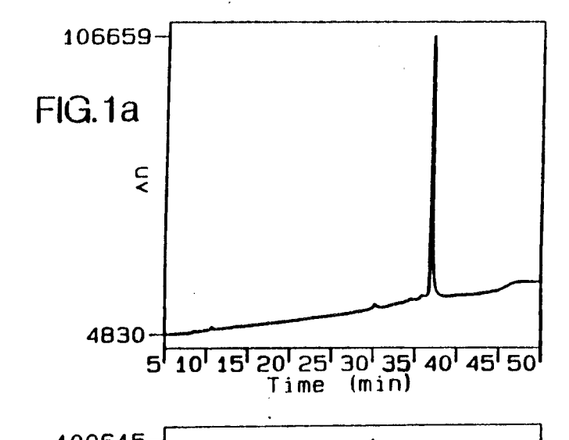
FIGS. 1a to 1d show traces from reverse phase HPLC conducted on samples of recombinant bFGF and its recombinant C78/96S analog with or without treatment with glutathione disulfide (GSSG).
Figure 1B:
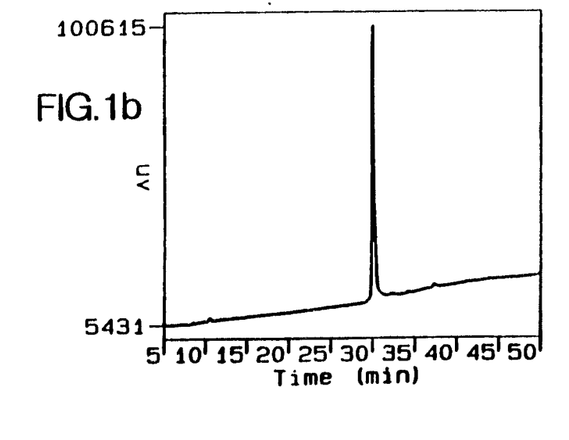

FIG. 1a shows the results of reverse phase HPLC run on a Vydac $C_{18}$ column before treatment as described above, using an acetonitrile/TFA gradient, under conditions shown in the figure. The elution time is between 35 and 40 minutes for the major peak.

After treatment as described above, the elution pattern of FIG. 1b is obtained, wherein the major elution peak is at roughly 30 minutes, showing that the treated bFGF is changed in form.

Figure 1C:
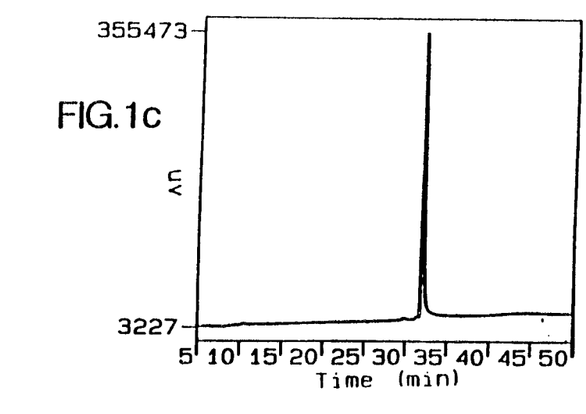
Figure 1D:
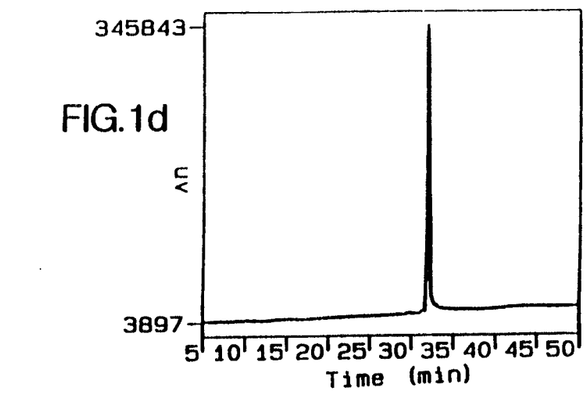

For comparison, FIGS. 1c and 1d show the elution patterns of an analog of the bFGF, which contains serines rather than cysteines at positions 78 and 96 as shown in the overplaced numbers of FIGS. 8 and 9. This analog elutes as a single peak at about 33 minutes, and treatment as described above has no effect on the elution pattern. The treatment method thus evidently 1) involves the cysteines at these positions and 2) has no apparent effect on analogs wherein these residues are not present.

Figure 2A:
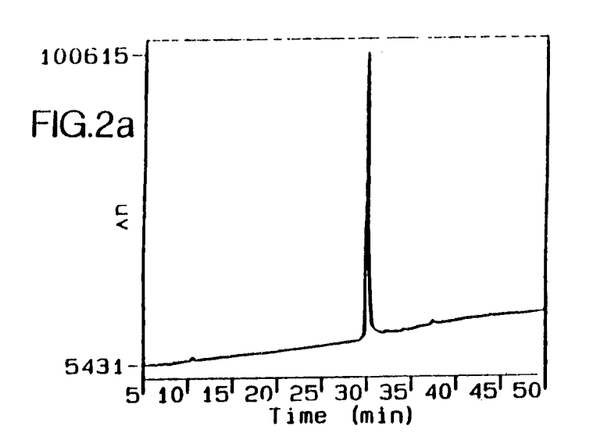
FIGS. 2a to 2c show traces of reverse phase HPLC conducted on GSSG-treated recombinant bFGF and bovine pituitary bFGF.
Figure 2B:
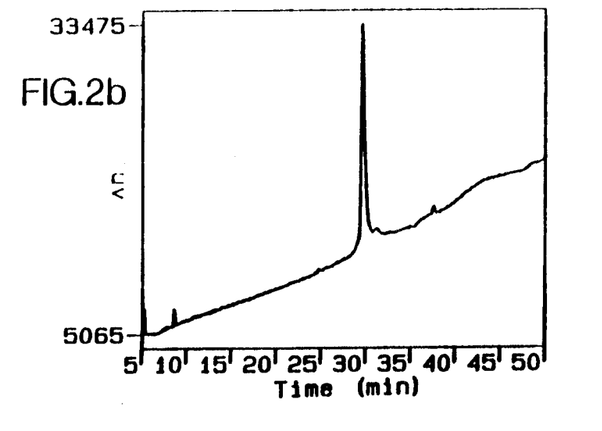
Figure 2C:
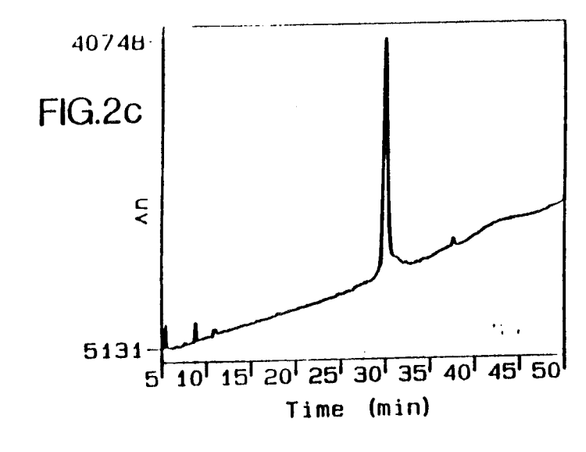

FIGS. 2a-2c show the results of reverse phase HPLC run on a Vydac $C_{18}$ column under conditions identical to those set forth above for FIGS. 1a-1d.

FIG. 2a shows a further example of the reverse phase HPLC analysis of the bFGF treated as in this Example in comparison with the behavior of material isolated from bovine pituitary by the procedure of Gospodarowicz. FIG. 2a shows the HPLC trace for the GSSG-treated recombinant bFGF; FIG. 2b shows the corresponding HPLC trace for the isolated material from pituitary; FIG. 2c shows the results of co-injection of the isolated and treated recombinant materials. The behavior of the recombinant bFGF treated with glutathione appears identical with that of the native isolated material.

Figure 3:
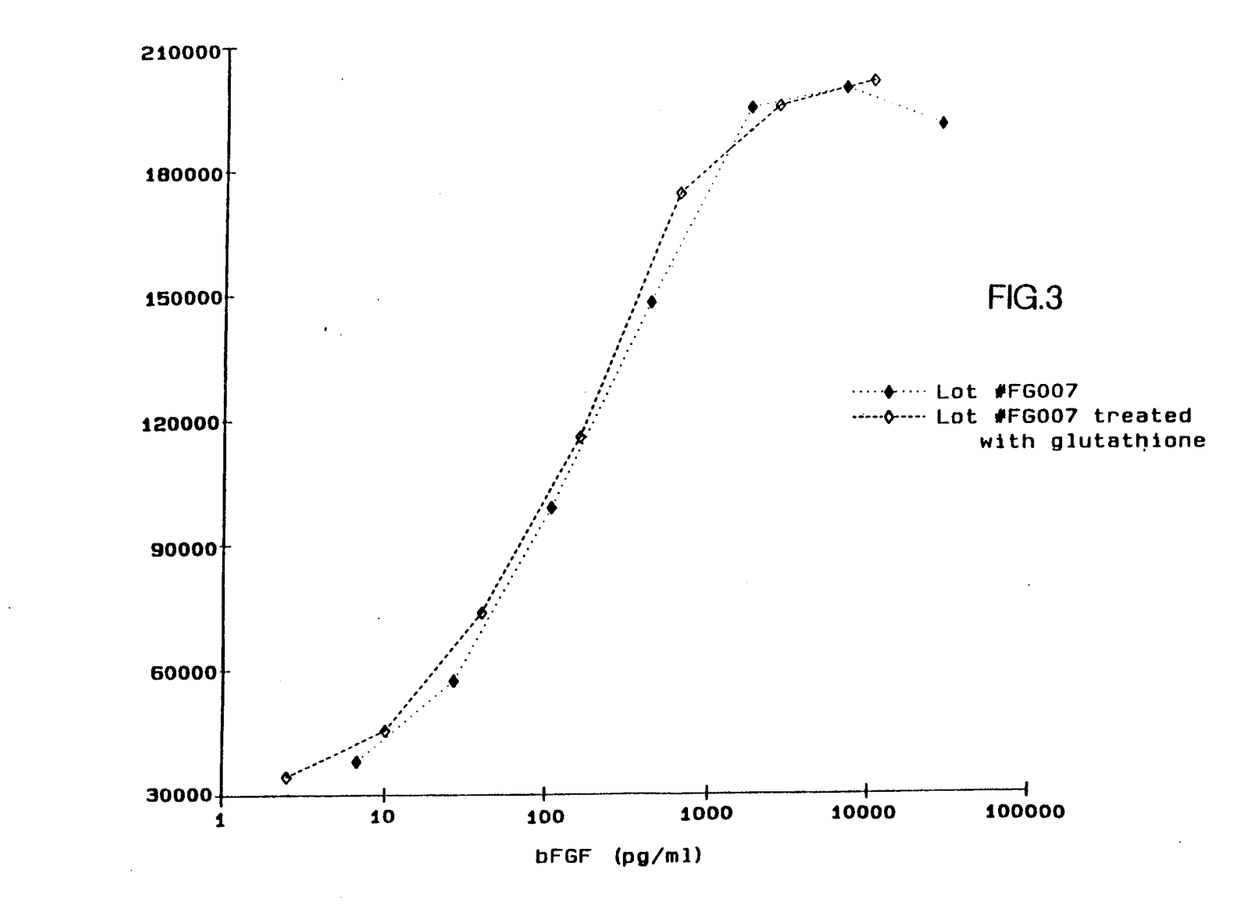
FIG. 3 shows the activity profiles for untreated recombinant bFGF and for bFGF treated with GSSG.

Finally, FIG. 3 shows the activity profiles in the ACE cell proliferation assay for untreated recombinant bFGF of Example 1 and for this bFGF treated with GSSG. No difference in activity is found.

EXAMPLE 2

Characteristics of GSSG-Treated Recombinant bFGF

Recombinant bFGF treated as described in Example 1 was incubated with I mM $CuCl_2$ for 1 min to accelerate, for experimental purposes, the multimerization which ordinarily occurs in untreated recombinant bFGF over time. The resulting bFGF was then subjected to reverse phase HPLC using heparin-TSK.

Figure 4A:
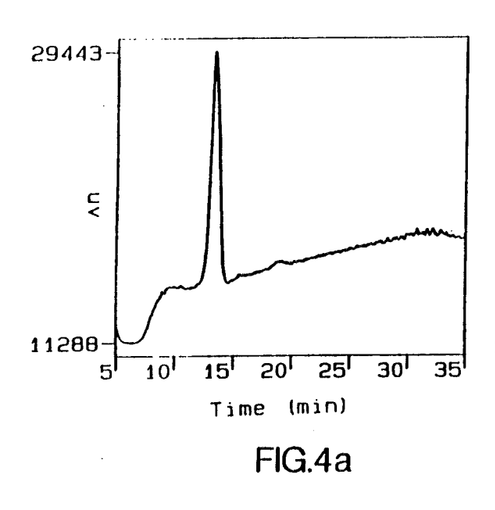
FIGS. 4a to 4f show a comparison of results of heparin-TSK HPLC chromatography of recombinant bFGF, which is untreated or treated with GSSG, and of bovine pituitary bFGF with or without prior treatment with cupric ion ($Cu^{+2}$).
Figure 4B:
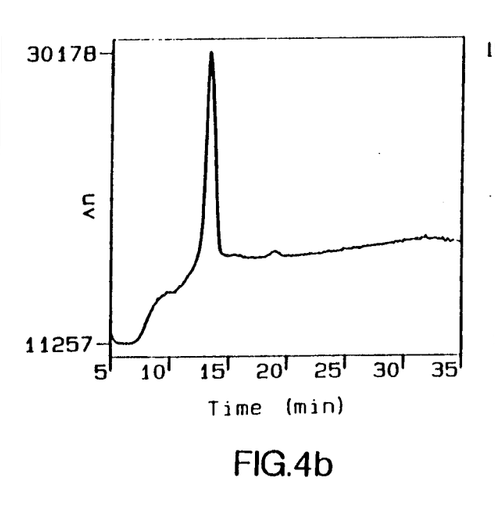
Figure 4C:
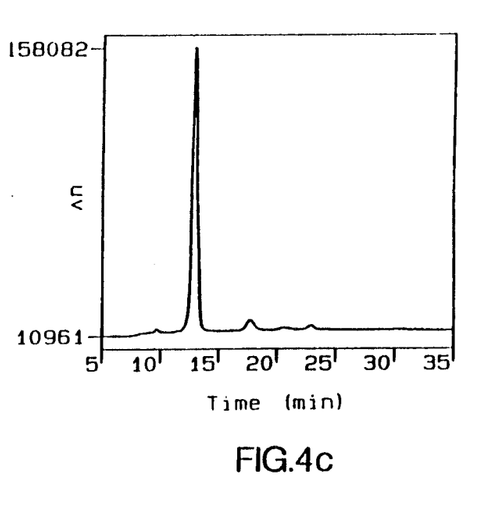
Figure 4D:
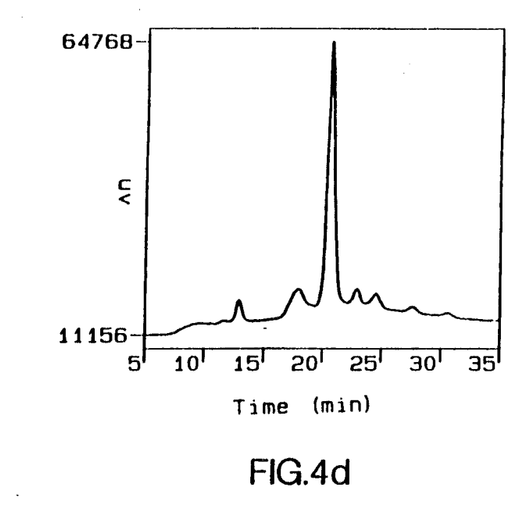

FIGS. 4a-4f, the heparin-TSK column is 7.5 mm×7.5 cm; eluants are A: 20 mM Tris, pH 7.5; B: 20 mM Tris, pH 7.5+3.0 M NaCl, and the gradient begins with 24% B for 1 minute followed by 40% B for 23 minutes followed by 100% B for 5 minutes and at a flow rate of 1 ml/minute with absorbance read at 220 nm. FIGS. 4a and 4b show that treatment with $Cu^{+2}$ has no effect on the chromatographic pattern of native bFGF isolated from bovine pituitary. However, as shown in FIGS. 4c and 4d, treatment with $Cu^{+2}$ of recombinant bFGF which has not been stabilized with GSSG results in a multiplicity of peaks and longer retention times.

Figure 4E:
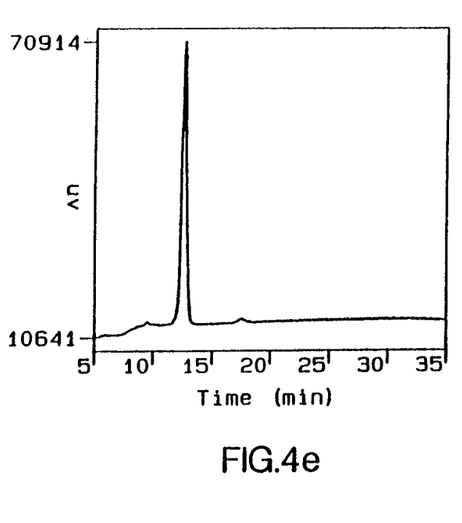
Figure 4F:
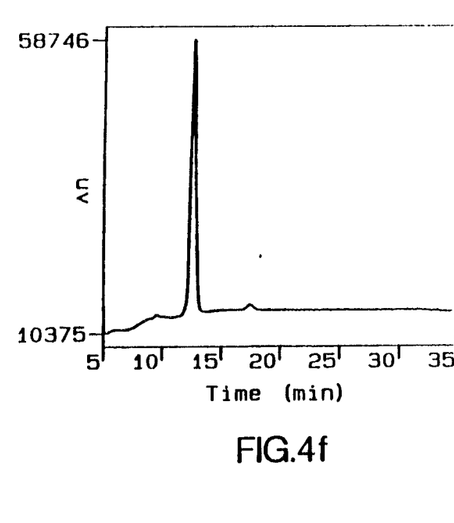
Figure 5A:
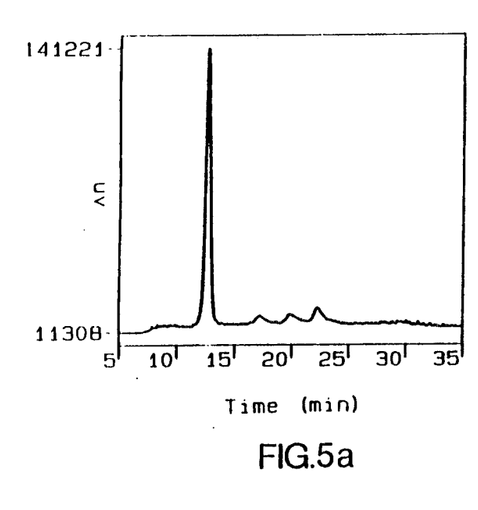
FIGS. 5a to 5f show the results of a series of heparin TSK HPLC chromatographies on bFGF untreated and treated with GSSG over a 5 day time period.
Figure 5B:
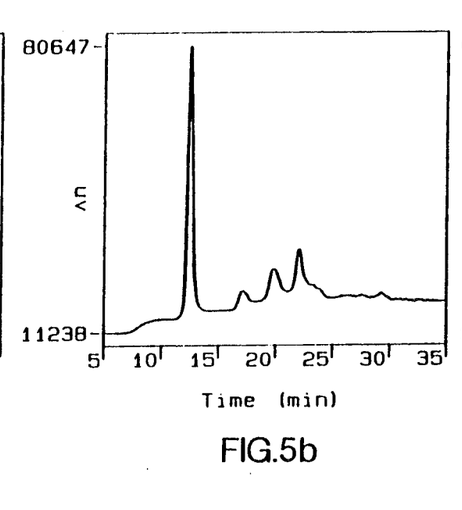
Figure 5C:
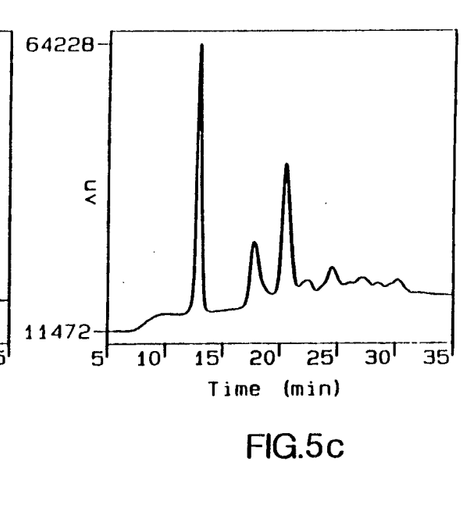
Figure 5D:
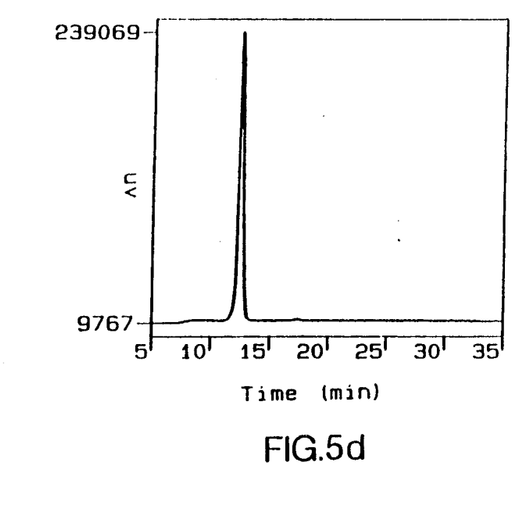
Figure 5E:
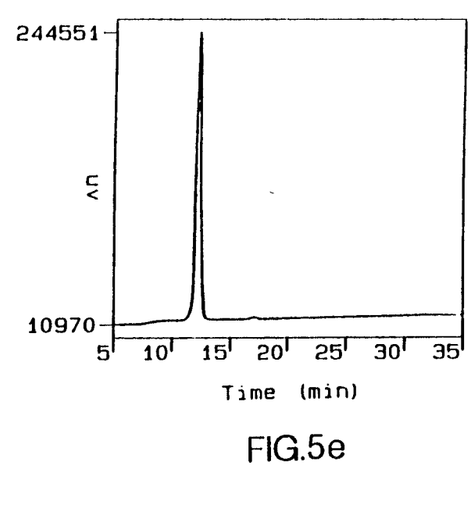
Figure 5F:
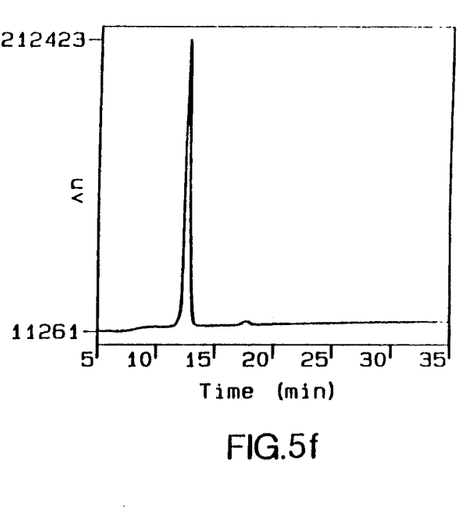

FIGS. 4e and 4f show the behavior of recombinant bFGF stabilized with GSSG, which is, like the native form, unaffected by treatment with $Cu^{+2}$.

The stabilized bFGF prepared in Example 1 is stable over at least a 5-day period, as shown in FIG. 5. The chromatography conditions in FIG. 5 are identical to those set forth in FIG. 4, described above. FIGS. 5d-5f are a series of HPLC traces derived from chromatography on heparin-TSK performed on the stabilized material. As indicated, in this series of figures, there is no change over the 5-day period. Under the same conditions untreated bFGF forms multimers and shows significant loss of the starting material, FIGS. 5a-5e.

EXAMPLE 3

Treatment with Cystine

Figure 6A:
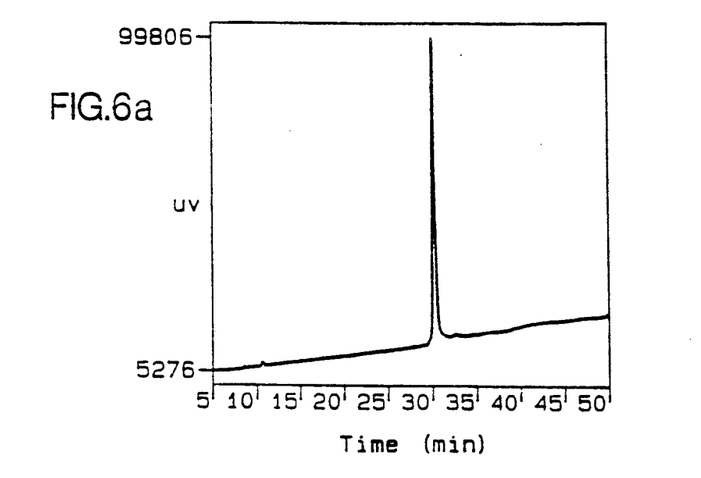
FIG. 6a to 6b show the results of reverse phase HPLC recombinant bFGF treated with cystine, as compared to native bovine pituitary bFGF.
Figure 6B:
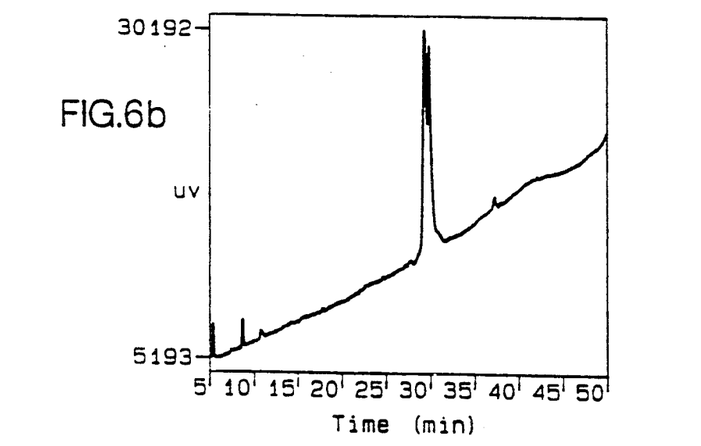

The procedure of Example 1 was followed except that 1 mM cystine was substituted in the incubation mixture for 1 mM glutathione disulfide and the reaction was performed at pH 7.0. The chromatorgraphy conditions in FIG. 6 represent chromatorgraphy on a Vydac $C_{18}$ column, 4.3 mm×25 cm, 5 μm particle size, 300 Å pore size with eluants A:0.1% TFA, B: acetonitrile+0.1% TFA and a gradient at 20% B for 40 minutes followed by 40% B for 5 minutes and at a flow rate of 1 ml/minute with absorbance read at 220 nm. FIG. 6a shows the results of reverse-phase HPLC performed on a Vydac $C_{18}$ column with the stabilized bFGF treated in this manner. FIGS. 6b and 6c show that the cystine-treated bFGF does not precisely co-migrate with the bFGF material isolated from pituitary. Thus the cystine-treated material is apparently not identical in behavior with natural bFGF from bovine pituitaries.

EXAMPLE 4

Figure 7A:
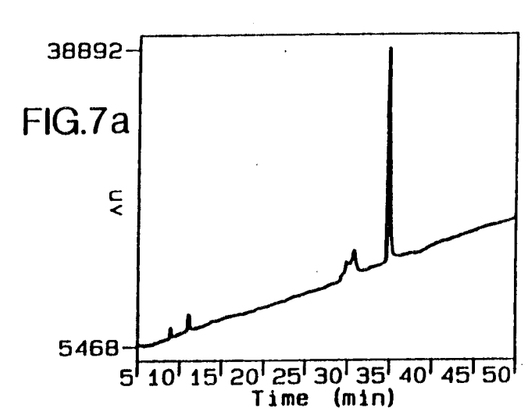
FIGS. 7a to 7d show the results of reverse phase HPLC conducted on recombinant bFGF analogs with and without prior treatment with GSSG.
Figure 7B:
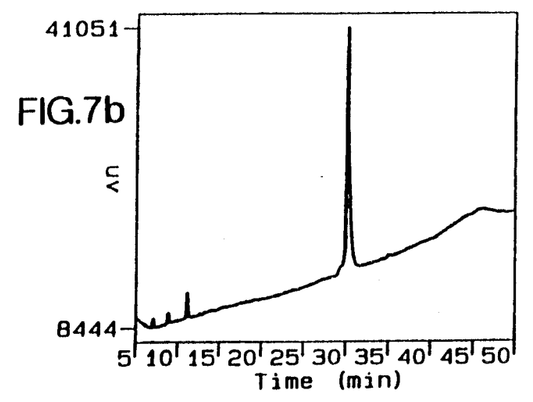
Figure 7C:
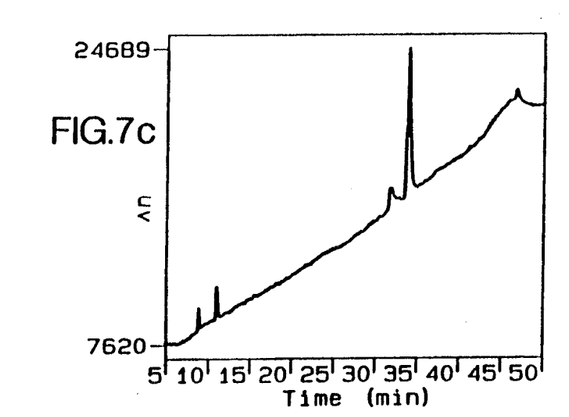
Figure 7D:
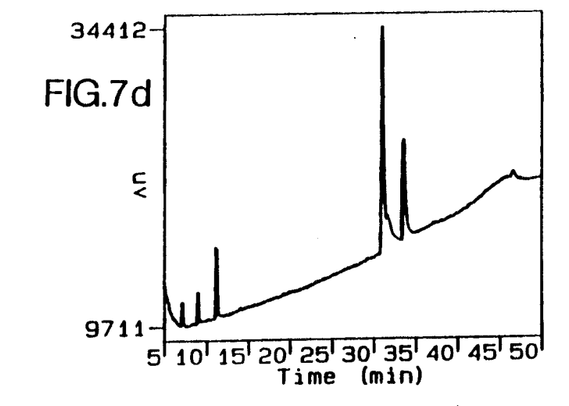

The procedure of Example 1 was followed to treat analogs of bFGF with GSSG. The procedure was identical except that the analog having a serine in place of cysteine at position 78 or at position 96 was substituted for the recombinant bFGF. The chromatorgraphy conditions shown in FIGS. 7a-7d are identical to those set forth in connection with FIG. 6 above. As shown in FIGS. 7a and 7b, this treatment results in a faster eluting peak in the case of the 78-Ser mutein, thus indicating the effect of GSSG on this analog. FIGS. 7c and 7d show similar results when the Ser-96 mutein is used (although the reaction is evidently not complete under these conditions).

I claim:

1. A method to stabilize and prevent multimerization of basic fibroblast growth factor proteins, which method comprises:

derivatizing a susceptible undenatured, reduced peptide having the amino acid sequence of basic fibroblast growth factor (bFGF) said bFGF containing at least one of the cysteines shown at position 78 and/or 96 as shown in the overlying numbers of FIGS. 8 and 9 or at a similar position in an analog, with an amount of a protective agent capable of forming a stable covalent S—S bond with at least one cysteine contained in said susceptible peptide without denaturing said peptide under conditions wherein and for a time sufficient to form said covalent S—S bond with said cysteine, said covalent bond of cysteine with said protective agent being effective to prevent multimerization of said bFGF.

said derivatizing being in the presence of a buffer of pH 6 or greater, said pH at which the bFGF does not denature.

2. The method of claim 1 wherein the protective agent is compound of the formula RSR wherein each R is independently an organic moiety of sufficient hydrophilicity to confer water solubility on said compound.

3. The method of claim 2 wherein the compound of the formula RSSR is selected from the group consisting of glutathione disulfide and cystine.

4. The method of claim 1 wherein the pH is pH 6–8.

5. The method of claim 1 which further includes the step of subjecting the treated bFGF to chromatographic purification.

6. Stabilized basic FGF prepared by the method of claim 1, with the proviso that when bFGF includes the amino acid sequence shown as residues 24–155 of the overplaced numbers shown in FIG. 8 or 9, the protective agent is not glutathione disulfide.

7. Stabilizied basic FGF prepared by the method of claim 5, with the proviso that when bFGF includes the amino acid sequence shown as residues 24–155 of the overplaced numbers shown in FIG. 8 or 9, the protective agent is not glutathione disulfide.

* * * * *